United States Patent [19]

Pfirmann

[11] Patent Number: 5,481,032

[45] Date of Patent: Jan. 2, 1996

[54] PROCESS FOR THE PREPARATION OF HALOGENATED BENZOIC ACIDS

[75] Inventor: Ralf Pfirmann, Griesheim, Germany

[73] Assignee: Hoechst Aktiengesellschaft, Frankfurt, Germany

[21] Appl. No.: 159,087

[22] Filed: Nov. 29, 1993

[30] Foreign Application Priority Data

Nov. 29, 1992 [DE]  Germany ................. 42 40 020.1

[51] Int. Cl.$^6$ ................................. C07C 229/52
[52] U.S. Cl. ................. 562/418; 562/419; 562/420; 562/421; 562/429; 562/430; 562/438; 562/474; 562/493
[58] Field of Search .................. 562/438, 474, 562/493, 429, 430, 438, 418, 419, 420, 421

[56] References Cited

PUBLICATIONS

Chambers et al., Tetrahedron Letters No. 32, pp. 2741–2742, 1970.
Smissman et al., Journal of Organic Chemistry, 33, pp. 4231–4236 (1968).
Journal of the American Chemical Society, Bd. 72, Nr. 12, Jan. 2, 1951, Washington, D.C.

Primary Examiner—Johann Richter
Assistant Examiner—John Peabody
Attorney, Agent, or Firm—Connolly & Hutz

[57] ABSTRACT

A process for the preparation of halogenated benzoic acids of formula (1):

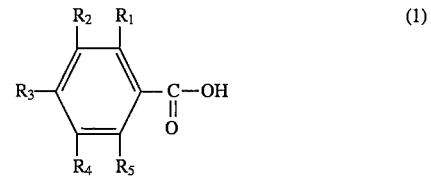

in which $R_1$, $R_2$, $R_3$, $R_4$ and $R_5$ are hydrogen, fluorine, chlorine or bromine atoms or $C_1$-$C_6$-alkyl, $C_1$-$C_6$-alkoxy, nitro, cyano, trifluoromethyl, aldehyde, $C_1$-$C_4$-alkoxycarbonyl, -$SO_2$-$C_1$-$C_4$-alkyl, -$SO_2$-phenyl, -$CONH_2$, -$CON(C_1$-$C_4$-alkyl$)_2$, hydroxy, carboxy, -$NH_2$ or -$N(C_1$-$C_4$- alkyl$)_2$ groups, at least one of the substituents $R_1$–$R_5$ being one of said halogen atoms, which comprises reacting 1 mol of a benzophenone, asymmetrically substituted on the benzene rings A and B, of general formula (2):

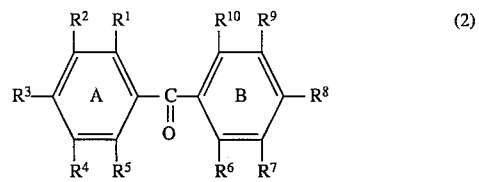

in which $R^1$–$R^{10}$ are as defined above for $R_1$–$R_5$, with about 1 to about 10 mol of an oxidizing agent selected from the group comprising hydrogen peroxide, urea/hydrogen peroxide addition product, an alkali metal peroxide, ammonium, alkali metal or alkaline earth metal peroxodisulfates, pertungstates, perborates or percarbonates, ozone, alkyl- or aryl-percarboxylic acids, alkyl- or aryl-persulfonic acids or persulfuric acid, at temperatures from about −20° to about +100° C.

16 Claims, No Drawings

PROCESS FOR THE PREPARATION OF HALOGENATED BENZOIC ACIDS

The present invention relates to a novel advantageous process for the preparation of halogenated benzoic acids and, if appropriate, of halogenated phenols from halogenated, especially fluorinated, benzophenones, if appropriate in one process step. Some of the halogenated benzophenones used as starting compounds are known and some are novel. The novel starting compounds and their preparation are described as follows. The novel asymmetric halogenated benzophenones are of the general formula (A):

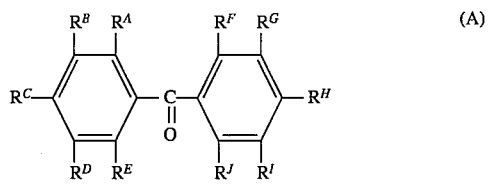

in which $R^A$, $R^B$, $R^C$, $R^D$ and $R^E$ are hydrogen, fluorine, chlorine or bromine atoms, except that at least one of the substituents $R^A$–$R^E$ is not a hydrogen atom, and $R^F$, $R^G$, $R^H$, $R^I$ and $R^J$ are hydrogen, fluorine, chlorine or bromine atoms, nitro, $C_1$-$C_4$-alkyl or $C_1$-$C_4$-alkoxygroups or phenyl or naphthyl groups which can be substituted on the aromatic ring by fluorine, chlorine or bromine atoms or nitro $C_1$-$C_4$-alkyl, $C_1$-$C_4$-alkoxy, -$CF_3$, -CHO, -CO- phenyl, -$SO_2$-phenyl, -CO-$C_1$-$C_4$-alkyl, -CO-$C_1$-$C_4$-alkoxy or -$SO_2$-$C_1$-$C_4$-alkyl groups, it being possible for up to 3 of the substituents $R^F$–$R^J$ to be $C_1$-$C_4$-alkyl groups, $C_1$-$C_4$-alkoxy groups or said aryl groups and for at most one of the substituents $R^F$–$R^J$ to be a nitro group, and the number of halogen atoms and nitro groups $R^F$–$R^J$, minus the number of $C_1$-$C_4$-alkyl, $C_1$-$C_4$ and aryl groups $R^A$ to $R^E$ being at least one less than the number of halogen atoms $R^A$ to $R^E$.

The process for their preparation is acylating 1 mol of a halogenated benzene of general formula (B):

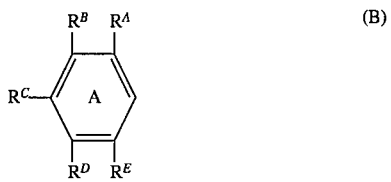

in which $R^A$, $R^B$, $R^C$, $R^D$ and $R^E$ are hydrogen, chlorine, fluorine or bromine atoms, with the proviso that at least one of the substituents $R^A$ to $R^E$ is one of said halogen atoms, with about 1 to 5 mol, preferably about 1.05 to about 2 mol, of a benzoyl halide of general formula (C):

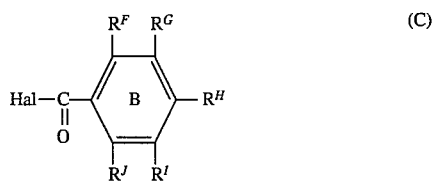

in which Hal is a fluorine, chlorine or bromine atom and $R^F$, $R^G$, $R^H$, $R^I$ and $R^J$ are as defined above, with the proviso that up to 3 of the substituents $R^F$–$R^J$ can be $C_1$-$C_4$-alkyl groups, $C_1$-$C_4$-alkoxy groups or said aryl groups and at most one of the substituents $R^F$–$R^J$ can be a nitro group, the number of halogen atoms and nitro groups $R^F$ to $R^J$, minus the number of $C_1$-$C_4$-alkyl, $C_1$-$C_4$-alkoxy and aryl groups $R^F$–$R^J$, being at least 1 less than the number of halogen atoms $R^A$–$R^E$, in the presence of an acylation catalyst, at temperatures from about 0° to about 230° C., preferably from about 70° C. to about 150° C.

The reaction is conducted in the absence or presence of an organic solvent which is inert towards the reactants, and, if appropriate, the process continues by reacting the resulting benzophenones of said formula (1), provided at least one of the substituents $R^A$–$R^J$ is a chlorine atom, if appropriate after intermediate isolation thereof, with about 1 to about 2.5 mol, preferably about 1.01 to about 1.5 mol, and particularly preferably about 1.05 to about 1.2 mol. of potassium, rubidium or cesium fluoride, or mixtures thereof, per chlorine atom to be exchanged.

The reaction is conducted at temperatures from about 120° to about 280° C., preferably from about 160° C. to about 230° C., in the absence or presence of a phase transfer catalyst and in the absence or presence of a dipolar aprotic solvent. The halogenated benzoic acids and halogenated phenols which can be prepared according to the invention are intermediates and can be converted to pharmaceuticals, plant protection agents and liquid-crystalline compounds by processes known in the literature. Compared with known processes, the process according to the invention has economic and ecological advantages since it employs only a few, relatively simple reaction steps and favorable reagents, some of which can also be recycled.

It is known that halogenated benzoic acids, for example 2,4,5-trifluorobenzoic acid, are suitable precursors for quinolonecarboxylic acid derivatives having antibacterial activity (German patent application A-3 318 145; European patent application A-340 055; Japanese patent 01/128 978). The process according to the invention represents an economically favorable alternative to the known processes for the preparation of, for example, 2,4-dichloro-5-fluorobenzoic acid, 2-chloro-4,5-difluorobenzoic acid, 2-chloro-4-fluorobenzoic acid and 2,3,4,5-tetrafluorobenzoic acid, as well as 2,4-dichloro-phenol, 2,6-difluorophenol, 2-fluorophenol and 4-fluorophenol. 2,4-dichloro-5-fluorobenzoic acid can be converted to fluoroquinolonecarboxylic acids having antibacterial activity by methods known in the literature (German Offenlegungsschrift 3 702 393; German Offenlegungsschrift 3 615 767; German Offenlegungsschrift 3 601 567; German Offenlegungsschrift 3 517 535; German Offenlegungsschrift 3 142 854). For 2-chloro-4,5-difluorobenzoic acid, such reactions are described in European patent application A-342 849 and European patent application A-321 191. 2,3,4,5-tetrafluorobenzoic acid is converted to highly active antibacterial agents as described in European patent application A-153 163, German Offenlegungsschrift 3 517 535, German Offenlegungsschrift 3 409 922 and German Offenlegungsschrift 3 318 145. 2,6-difluorophenol can be converted to solid conductive polymers (Japanese patent 01/170 010) for the construction of capacitors, and also to monomers (European patent application A-308 863), herbicides (European patent application A-142 328; U.S. Pat. No. 4,750,931), insecticides and acaricides (British patent 2 187 452; British patent 2 199 825) and compounds having antiviral activity (J. Med. Chem. 32 (2) [1989], 450–455, G. D. Diana). 4-fluorophenol can be used by methods known in the literature to prepare, inter alia, antiarrhythmics (European patent application A-454 498), phospholipase inhibitors (U.S. Pat. No. 5,070,207), fungicides and psychoactive substances (European patent application A-449 187; European patent application A-428 437), drugs for arthritis and osteoporosis (European patent application A-403 185, Robins Co.), diuretics, antihypertensives, anticoagulants and lipoxygenase inhibitors (French patent 2 653 119) and liquid-crystalline compounds (European patent application A-442 306). 2-fluorophenol can be converted by described methods to, for example, special dyes (Japanese patent 03/255 086, ferroelectric liquid crystals (Japanese patent 03/197 438), psychotropic compounds (European patent application A-428 437), antispasmodics (U.S. Pat. No. 5,025,031) and substances active on the central nervous system (European patent application A-417 027). 2-chloro-4-fluorophenol can be used for example to prepare advantageous herbicides (Japanese patent 02/048 571; European patent application A-271 170) and fungicides (European patent application A-326 330). 3-chloro-4-fluorophenol is used for example for the preparation of drugs for treating diabetes (European patent application A-230 379) and precursors for liquid crystals (Japanese patent 59/210 048; Japanese patent 59/175 453). For 2-chloro-4-fluorobenzoic acid, methods are known which allow conversion to cholesterol biosynthesis inhibitors (European patent application A-431 480) and herbicides (Synthesis (1987), 883–887, T. N. Wheeler et al.; PCT International patent application 8 707 602). 2,4-dichlorophenol can be used for example for the preparation of anthelmintics and antiseptics (French patent 2 658 192), herbicides (Japanese patent 03/193 771), polymers with absorption properties for ultraviolet light (Japanese patent 03/200 788) and molecular probes for detecting the hydrolysis properties of enzymes (Japanese patent 03/215 462).

The advantages of the process according to the invention over the processes known hitherto for the preparation of valuable halogenated benzoic acids will now be illustrated using 2-chloro-4,5-difluorobenzoic acid as an example.

A chlorine/fluorine exchange (halex) reaction of 2,4-dichloro-5-fluorobenzonitrile (European patent application A-431 373) in the industrially undesirable solvent dimethyl sulfoxide using spray-dried potassium fluoride gives 2-chloro-4,5-difluorobenzonitrile, which can be converted to the benzoic acid by methods known in the literature (Houben-Weyl-Müller, Methoden der Organischen Chemie (Methods of Organic Chemistry), vol. VIII (1952), pp. 429–433). In this case, even when the reaction is carried out using less active solvents such as sulfolane (European patent application A-433 124), 2,4,5-trifluorobenzonitrile is obtained as a by-product in yields of around 20%, leading to increased fluoride consumption and a greater degree of decomposition. Even more unfavorable in this case, however, is the proportion of 4-chloro-2,5-difluorobenzonitrile contained in the 2-chloro-4,5-difluorobenzonitrile, which amounts to between about 3% and about 8%, depending on the conversion, and has to be separated off by an expensive process. The 2,4-dichloro-5-fluorobenzonitrile itself must be prepared by an expensive process (European patent application A-433 124) involving the bromination of 2,4-dichlorofluorobenzene and subsequent bromine/nitrile exchange by means of alkali metal cyanides.

Selective chlorine/fluorine exchange of the 4-chlorine atom in 2,4-dichloro-5-fluorobenzoic acid esters is also known (European patent application A-355 774), but the preparation of the starting materials is very unfavorable, especially because only higher and branched esters give satisfactory yields in the exchange reaction. In the case of lower alkyl esters, which are more readily accessible, poor yields are obtained due to a high degree of decomposition at the reaction temperature, because the ester grouping brings only slight activation but is reactive towards nucleophiles.

The fluorination of 4,5-dichlorophthalic anhydride (German Offenlegungsschrift 3 303 378; European patent application A-55 630; European patent application A-55 629; Japanese patent 02/76 872) gives 4,5-difluorophthalic anhydride, which can be converted to 4,5-difluoroanthranilic acid by reaction with ammonia and a Hofmann degradation (European patent application A-55 630; U.S. Pat. No. 4,994,606) and to 2-chloro-4,5-difluorobenzoic acid by a chlorinating Sandmeyer reaction (Japanese patent 02/215 744). The decarboxylation of 4,5-difluorophthalic acid by a variety of methods (European patent application A-429 848; Japanese patent 01/25 737; Japanese patent 63/295 529) can give 3,4- difluorobenzoic acid, which can be converted to the target product by nitration and denitrating chlorination (U.S. Pat. No. 5,003,103). These alternative syntheses are unfavorable, partly because they involve many steps and give poor overall yields, and partly because of problems with materials and difficulties of reaction technique.

In general, acylations of 1,2,4-trifluorobenzene and 3,4-difluorochlorobenzene by means of acetyl chlorides, which under certain circumstances are aliphatically chlorinated, and a subsequent haloform reaction by means of hypochlorite solutions (European patent application A-411 252; German patent 3 840 371; German patent 3 840 375; European patent application A-303 291) are economically unfavorable because 1,2,4-trifluorobenzene and 3,4-dichlorofluorobenzene (via 1,2-difluorobenzene by chlorination, or starting from 2,5-dichloronitrobenzene [T. F. Braish et al., Org. Prep. Proced. Int. 23 (1991), 655–658], or the denitrating chlorination of 3,4-difluoronitrobenzene) must themselves be prepared by very expensive steps, such as a Balz-Schiemann reaction, with high losses of yield, and the degradation reactions contaminate the effluent with large amounts of salts.

The reaction according to the invention is based on a type of reaction known in the literature, namely the Baeyer-Villiger oxidation (Baeyer, Villiger, Ber. 32 (1899), 3625). In this reaction, a ketone, or more rarely an aldehyde, is reacted with peracids under various reaction conditions (Baeyer, loc. cit.; W. Dilthey, Ber. (1939), 219–237; Wacek, Bezard, Ber. 74 (941), 845; Wittig, Pieper, Ber. 73 (1940), 295). A conversion to esters is observed macroscopically and is explained microscopically by the anionotropic migration of a carbonyl group residue. It is known that methyl groups and hydrogen atoms have a very low tendency to migrate, and this also has industrial application. The reaction of simple asymmetrical ketones, especially benzophenones, has already been investigated by W. v. E. Doering et al. (J. Am. Chem. Soc. (1950), 5515–5518), although the selectivities as well as the yields and conversions were low in some cases because it was the authors' intention to examine mechanistic aspects. In particular, the reaction of polyhalogenated benzophenones had not yet been investigated. An earlier reference to the selectivity of such reactions in the presence of nitro groups can be found in Ber. 71 (1938) (W. Dilthey et al.). According to this study, 4-nitrobenzoic acid and phenol are obtained from 4-nitrobenzophenone.

The invention relates to a novel advantageous process for the preparation of halogenated benzoic acids of general formula (1):

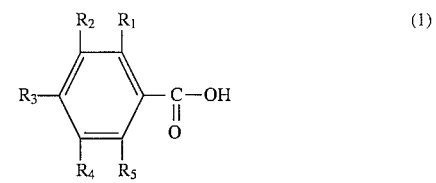

in which $R_1$, $R_2$, $R_3$, $R_4$ and $R_5$ are hydrogen, fluorine, chlorine or bromine atoms or $C_1$-$C_6$-alkyl, $C_1$-$C_6$-alkoxy, nitro, cyano, trifluoromethyl, aldehyde, $C_1$-$C_4$-alkoxycarbonyl, -$SO_2$-$C_1$-$C_4$-alkyl, -$SO_2$-phenyl, -$CONH_2$, -$CON(C_1$-$C_4$-alkyl$)_2$, hydroxy, carboxy, -$NH_2$ or -$N(C_1$-$C_4$- alkyl$)_2$ groups, at least one of the substituents $R_1$–$R_5$ being one of said halogen atoms, which comprises reacting 1 mol of a benzophenone, asymmetrically substituted on the benzene rings A and B, of general formula (2):

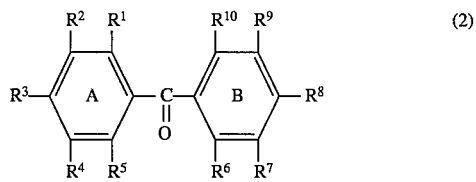
(2)

in which $R^1$–$R^{10}$ are as defined above for $R_1$–$R_5$, with about 1 to about 10 mol, preferably about 1.05 to about 3 mol, of an oxidizing agent selected from the group comprising hydrogen peroxide, urea/hydrogen peroxide addition product, alkali metal peroxides such as sodium peroxide, ammonium, alkali metal or alkaline earth metal peroxodisulfates, pertungstates, perborates or percarbonates, ozone, alkyl- or aryl-percarboxylic acids, alkyl- or aryl-persulfonic acids or persulfuric acid (Caro's acid), optionally in the presence of inorganic and/or organic solvents which are inert towards the reactants, at temperatures from about −20° to about 100° C, preferably from about 0° to about 70° C. and particularly preferably from about 20° to about 60° C., under atmospheric pressure, super atmospheric pressure or reduced pressure.

The following may also be mentioned specifically as suitable oxidizing agents:

sodium, potassium or ammonium peroxodisulfate, sodium percarbonate, performic acid, peracetic acid, trifluoroperacetic acid, hexafluoropropanepersulfonic acid, 3-chloroperbenzoic acid, 3,5-dinitroperbenzoic acid, magnesium monoperphthalate, methanepersulfonic acid, trifluoromethanepersulfonic acid, p-toluenepersulfonic acid or ®Oxone (= potassium peroxomonosulfate).

It is frequently convenient to carry out the reaction according to the invention in inorganic or organic solvents which are inert towards the reactants. Examples of such solvents are sulfuric acid of varying concentration, for example about 80 percent by weight sulfuric acid to about 20 percent by weight oleum, preferably about 95 percent by weight sulfuric acid to about 5 percent by weight oleum, and also hydrogen fluoride, aliphatic carboxylic acids having 1 to 6 carbon atoms which can be substituted by halogen atoms in the alkyl radical, alkylsulfonic acids having 1 to 6 carbon atoms which can be substituted by halogen atoms in the alkyl radical, or acetic anhydride.

Instead of one of the above-mentioned solvents or in addition thereto, i.e. in combination therewith, it is possible to use an inert organic solvent such as dichloromethane, trichloromethane, 1,2-dichloroethane, toluene, a xylene, chlorobenzene, dichlorobenzene, chlorotoluene or dichlorotoluene.

In the simplest, preferred mode of carrying out the process according to the invention, the reaction is performed in sulfuric acid of varying concentration and hydrogen peroxide is metered in. As a rule, sulfuric acid or oleum of the above-mentioned concentrations is used. The benzophenones to be reacted, of said general formula (2), can be dissolved in this medium without difficulty, between about 200 percent by weight and about 2000 percent by weight of sulfuric acid being used. Hydrogen peroxide solution is metered into this mixture. This is done using solutions containing about 10 to about 90 percent by weight of hydrogen peroxide, preferably commercially available solutions containing about 25 to about 50 percent by weight. The low concentration of these solutions has advantages in terms of handling and safety. More dilute solutions give rise to excessive heat production when metered in, because of the heat of hydration of sulfuric acid. It is self-evident that premixed sulfuric acid/hydrogen peroxide solutions give the same results. The reaction is carried out at the temperatures mentioned above. The reaction times are between 1 h and 16 h and in most cases between about 3 and about 8 h, depending on the benzophenone to be reacted. The metering times can be selected according to the heat production.

When the reaction is complete, the benzoic acids obtained can be isolated by dilution of the reaction mixture and filtration; extraction of the substance dissolved in water may be necessary. The phenols which may be formed in parallel can generally be isolated by steam distillation, most favorably after dilution of the reaction mixture (sulfuric acid concentration between about 50 and about 80 percent by weight) and, if appropriate, after heating for several hours to effect desulfonation (Gilbert, Sulfonation and Related Reactions, pp. 427–442). Extractive separation from the reaction mixture and subsequent separation of the reaction products by distillation also proceed without difficulty in most cases.

To prevent hydrogen fluoride corrosion, it can be prudent to work up fluorine-containing compounds in the presence of fluoride-trapping agents such as calcium salts or silicon dioxide. Examples of suitable calcium salts or compounds are calcium chloride, sulfate or hydroxide.

If asymmetrical benzophenones of said general formula (2) are used according to the invention, substituted benzoic acids and phenols are obtained under the conditions of the preferred embodiment described, without it being possible to detect substituted phenyl benzoates in a phase of the reaction. Surprisingly, only a combination of these products is obtained very selectively, because the different aryl residues have markedly different migration tendencies under the conditions according to the invention. A phenol is formed from the benzophenone residue which contains fewer electron-attracting substituents. It is possible here to apply the rule that electron-releasing groups, for example $C_1$-$C_4$-alkyl, $C_1$-$C_4$-alkoxy or aryl groups, are compensated in their effect, in terms of the invention, by the same number of electron-attracting groups, for example halogen atoms or nitro groups. An analogous argument can be applied to the other aryl residue, from which the corresponding halogenated benzoic acid is formed because of the lower migration tendency. This selectivity is observed in the process according to the invention and is a subject of the invention if the number of electron-attracting radicals in the ring A is at least 1 greater than the number of electron-attracting radicals, minus the number of alkyl or alkoxy groups, in the ring B.

The following Examples serve to illustrate the process according to the invention without implying a limitation.

EXAMPLE 1

26.8 g (0.1 mol) of 2,4-dichloro-5-fluorobenzophenone are dissolved in 250 g of 96% sulfuric acid, and 17 g of 30% hydrogen peroxide solution are added at 0° C., with thorough mixing, in such a way that the temperature does not exceed 40° C. When the metered addition is complete, the temperature is allowed to drop to 20° C. and the mixture is stirred for 5 h at this temperature. If the conversion is incomplete, a further 5 g of hydrogen peroxide solution are metered in (T<40° C.) and the mixture is diluted with 1000 g of water after a further 3 h of reaction time and is subsequently stirred for 2 h. The 2,4-dichloro-5-fluorobenzoic acid which has precipitated out is filtered off and purified by recrystallization (water) to give 17.8 g (0.0852 mol, 85%) of 2,4-dichloro-5-fluorobenzoic acid melting at 144°–146° C.

EXAMPLE 2

32 g of 20% hydrogen peroxide solution are added dropwise over 30 min to a solution of 37.8 g (0.15 mol) of 2-chloro-4,5-difluorobenzophenone in 400 g of 100% sulfuric acid in such a way that the temperature remains below 35° C. The reaction is complete after 7 h. The reaction mixture is then poured on to 1200 g of ice. Extraction of the mother liquor with methyl tert-butyl ether, isolation of the crude product from the extract and crystallization from water gives 17.0 g (0.0883 mol, 88%) of colorless 2-chloro-4,5-difluorobenzoic acid melting at 104.4°–105.8° C.

EXAMPLE 3

28.7 g (0.1 mol) of 2,4-dichloro-4',5-difluorobenzophenone are dissolved in 250 g of 10% oleum, and 25 g of 50% hydrogen peroxide solution are added at temperatures up to 30° C. When the metered addition has ended (30 min), the mixture is heated for 8 h at 50° C. and, after cooling, is poured on to 250 g of ice. This mixture is kept for 8 h at 140° C. and 4-fluorophenol is then recovered by steam distillation (7.5 g, 0.0673 mol, 67%, m.p. (DSC) 42.6° C.). 2,4-dichloro-5-fluorobenzoic acid is isolated as described in Example 1 (17.0 g, 0.0813 mol, 81%, m.p. 143°–145° C.). (DSC = differential scanning calorimetry)

EXAMPLE 4

11 g of 90% hydrogen peroxide solution are added dropwise at 0°–10° C. to 61.0 g (0.25 mol) of 2,4-dichloro-2'(4')-methylbenzophenone in 300 g of 90% sulfuric acid. The mixture is subsequently stirred for 4 h and poured on to 800 g of ice. 39.2 g (0.206 mol, 83%) of beige-colored 2,4-dichlorobenzoic acid (melting point 151°–157° C.) are isolated by filtration. A mixture of o- and p-cresol (24.5 g) can be isolated by heating of the aqueous phase at 120° C. (6 h) and steam distillation.

EXAMPLE 5

If 59.0 g (0.25 mol) of 2,4,5-trifluorobenzophenone are used with 53.3 g of 20 percent hydrogen peroxide solution and the procedure is otherwise as indicated in Example 2, 34.7 g (0.197 mol, 79%) of 2,4,5-trifluorobenzoic acid melting at 99.6°–101.6° C. are obtained.

EXAMPLE 6

If 60.5 g (0.2 mol) of 2,4,5-trichloro-2'-fluorobenzophenone and 50 g of 50 percent hydrogen peroxide solution are used and the reaction is otherwise carried out as described in Example 3, 40.8 g (0.18 mol, 90%) of 2,4,5-trichlorobenzoic acid (crude, purity (GC) ca. 85%, melting point 158°–165° C.) and 12.3 g (0.11 mol, 55%) of 2-fluorophenol (purity (GC)>97%) are isolated by filtration after dilution and stirring of the mother liquor (2 h).

EXAMPLE 7

33.7 g (0.1 mol) of 2,3,4,5-tetrachloro-2'(4')-fluorobenzophenone were added to 500 g of 96% sulfuric acid, and 25 g (0.22 mol) of 30% hydrogen peroxide solution were added to the dark brown solution at 20° C., the temperature being kept constant at 55° C. After a further 9 h at 60° C., the mixture was poured on to 500 g of ice and refluxed for 6 h. Subsequent steam distillation gives a mixture of 0.7 g (0.006 mol, 6%) of 2-fluorophenol and 6.4 g (0.57 mol, 57%) of 4-fluorophenol. If the batch size is increased, the phenols can be separated by fractionation, 2-fluorophenol passing over at 150°–155° C. and 4-fluorophenol at 177°–182° C. (101.3 KPa). After cooling, 2,3,4,5-tetrachlorobenzoic acid is obtained as a light brown solid (24.1 g, crude, melting point 186°–192° C.) by filtration of the mother liquor.

EXAMPLE 8

2,3,5,6-tetrachlorobenzoic acid was obtained in suspension by the reaction of 37.1 g (0.1 mol) of 2,2',3,5,6-pentachloro-4'-fluorobenzophenone in 350 g of 100% sulfuric acid with 20 g (0.176 mol) of 30% hydrogen peroxide solution at 60° C. (8 h) and subsequent dilution with water (500 g), and was filtered off (23.2 g, 0.089 mol, 89%, melting point 171°–178° C. (crude)). 10.3 g (0.070 mol, 70%) of colorless 2-chloro-4-fluorophenol (f.p. 21.4° C.) are isolated by heating of the filtrate at 150° C. (4 h) and steam distillation in the presence of 10 g of calcium chloride.

EXAMPLE 9

If the procedure described in Example 8 is followed, except that 30.7 g (0.1 mol) of 3'-chloro-2,3,4,4',5-pentafluorobenzophenone are used, 8.5 g (0.058 mol, 58%) of 3-chloro-4-fluorophenol are obtained after steam distillation and 15.4 g (0.079 mol, 79%) of light brown 2,3,4,5-tetrafluorobenzoic acid are obtained by extraction with methyl tert-butyl ether and concentration of the extract from the mother liquor. Said acid can be purified by recrystallization from water (m.p. 85.5°–86° C.).

EXAMPLE 10

If the procedure described in Example 8 is followed (reaction temperature 70° C.) using 35.6 g (0.1 mol) of 2,3,4,5-tetrachloro-2',6'-difluorobenzophenone, 3.1 g (0.024 mol, 24%) of 2,6-difluorophenol and 22.4 g (0.086 mol, 86%) of 2,3,4,5-tetrachlorobenzoic acid (crude, purity (GC) ca. 95%) are obtained.

EXAMPLE 11

A mixture of the isomers 2-chloro-3,4,5-trifluorobenzoic acid and 5-chloro-2,3,4-trifluorobenzoic acid in a ratio of 1:1.5 (24.1 g, 0.114 mol, 76%) is obtained from 45.8 g (0.15 mol) of 2(5),2'-dichloro-3,4,5(2)-trifluorobenzophenone under the conditions of Example 8 using 30 g of 30 percent hydrogen peroxide solution, and 8.7 g (0.068 mol, 45%) of 2-chlorophenol are obtained after steam distillation.

EXAMPLE 12

The reaction of 35.8 g (0.1 mol) of 2-bromo-4-chloro-5-fluoro-3'-nitrobenzophenone in 150 g of 5% oleum with 9.7 g (0.2 mol) of 70% hydrogen peroxide solution gives a mixture (29.0 g) of 2-bromo-4-chloro-5-fluorophenol, 2-bromo-4-chloro-5-fluorobenzoic acid, 3-nitrophenol and 3-nitrobenzoic acid (proportions in GC area-%: 14, 35, 36, 15) after dilution (300 g of water), refluxing for 4 h and extraction with methyl tert-butyl ether after removal of the solvent.

EXAMPLE 13

30.8 g (0 1 mol) of 2-bromo-4-fluoro-3',5'-dimethylbenzophenone were dissolved in 140 g of 90% sulfuric acid, and 5.7 g of 90% hydrogen peroxide solution were added dropwise (metering time 1 h) between −10° C. and 0° C. After subsequent stirring for 2 h, the mixture was poured on to 500 g of ice and then heated at the boil for 5 h. Isolation as described in Example 8 gave 9.6 g (0.079 mol, 79%) of 3,5-dimethylphenol and 15.6 g (0.071 mol, 71%) of 2-bromo-4-fluorobenzoic acid (crude, purity (GC) ca. 90%, melting point 160°–166° C.)

EXAMPLE 14

If the reaction is carried out using 27.6 g (0.1 mol) of 2,4-difluoro-3',5'-dimethoxybenzophenone and the procedure is otherwise as described in Example 13, 12.4 g (0.081 mol, 81%) of 3,5-dimethoxyphenol and 13.2 g (0.084 mol, 84%) of 2,4-difluorobenzoic acid (m.p. 183°–185° C.) are obtained.

EXAMPLE 15

If the procedure is as described in Example 13, except that 50.1 g (0.175 mol) of 2,3-dichloro-4,4'-difluorobenzophenone and 10 g of 90 percent hydrogen peroxide, solution are used, 11.8 g (0.105 mol, 60%) of 4-fluorophenol and 28.3 g (0.136 mol, 78%) of 2,3-dichloro-4-fluorobenzoic acid are obtained.

EXAMPLE 16

30.9 g (0.125 mol) of 2-chloro-4-fluoro-4'-methylbenzophenone are converted to 19.6 g (0.112 mol, 90%) of 2-chloro-4-fluorobenzoic acid and 10.6 g (0.098 mol, 78%) of p-cresol as described in Example 13, using 7.1 g of 90 percent hydrogen peroxide solution.

EXAMPLE 17

23.5 g (0.1 mol ) of 3,4-difluoro-4' -methylbenzophenone can be converted to 11.9 g (0,075 mol, 75%) of 3,4-difluorobenzoic acid and 9.5 g (0.088 mol, 88%) of p-cresol as described in Example 13.

EXAMPLE 18

28.1 g (0.1 mol) of 2,5-dichloro-4'-methoxybenzophenone are converted to 15.8 g ( 0.083 mol, 83% ) of 2,5-dichlorobenzoic acid (melting point 150°–155.5° C.) and 5.0 g (0.04 mol, 40%) of hydroquinone monomethyl ether as described in Example 13.

EXAMPLE 19

7.9 g of 30% hydrogen peroxide solution and 20 g of formic acid were added dropwise at 20°–25° C., with stirring, to 5.4 g (20 mmol) of 2,4-dichloro-5-fluorobenzophenone (crude, 11% isomer content) in 40 g of 1,2-dichloroethane. The mixture was then heated at the boil for 20 h, further hydrogen peroxide/formic acid mixture being added after 10 h. The mixture was then diluted with 100 g of water, the phases were separated and the organic phase was dried over magnesium sulfate. After filtration and removal of the solvent, the residue was heated for 5 h at 120° C. with 50 g of 50% sulfuric acid (cleavage of the phenyl 2,4-dichloro-5-fluorobenzoate present) and then diluted with 100 g of water. The 2,4-dichloro- 5-fluorobenzoic acid which has precipitated out (2.8 g (crude), 13.4 mol, 68% based on content of pure material (GC)) can be purified by recrystallization from water.

EXAMPLE 20

8 g of ammonium peroxodisulfate are introduced into 5 g (19.8 mmol ) of 2-chloro-4,5-difluorobenzophenone and 20 g of glacial acetic acid and the mixture is heated at 90° C. (12 h). 100 g of 70% sulfuric acid are then added and the mixture is heated for 2 h at 150° C. Dilution with 200 g of water and filtration gives 3.1 g (16.0 mmol, 81%) of 2-chloro-4,5-difluorobenzoic acid (purity (GC) ca. 92%). Recrystallization from water gives 2.5 g of product melting at 104° C.–105° C.

EXAMPLE 21

2.1 g (20 mmol) of acetic anhydride were added dropwise at 0° C. to a mixture of 2.0 g (8 mmol) of 2-chloro-4-fluoro-4'-methylbenzophenone, 9.9 g (0.07 mol) of disodium hydrogenphosphate and 3.8 g (40 mmol) of urea/hydrogen peroxide adduct in 50 ml of dichloromethane. The resulting mixture was then allowed to warmup to room temperature. After 12 h at 20° C., it was neutralized with sodium hydrogencarbonate solution and the aqueous phase was subsequently extracted with dichloromethane. The solvent was then distilled off from the organic phase under vacuum. 50 g of 70% sulfuric acid were added to the residue (2.5 g, containing ca. 80% of phenyl 2-chloro-4-fluorobenzoate) and the mixture was heated for 6 h at the boiling point. Dilution of the cooled mixture, extraction with methyl tert-butyl ether, drying, removal of the solvent and recrystallization of the crude product from water gives 1.0 g (5.7 mmol, 72%) of 2-chloro-4-fluorobenzoic acid in the form of a colorless powder (m.p. 182°–186° C.).

EXAMPLE 22

2.3 g (10 mmol) of 2-methyl-4-fluoro-4'-methylbenzophenone were added dropwise at 20° C., under inert gas, to 3.8 g (12 mmol) of 3-chloroperbenzoic acid (55%) in 40 ml of dichloromethane and 14.2 g (0.1 mol) of disodium hydrogenphosphate and the reaction mixture was then heated for 8 h at 40° C. It was monitored by gas chromatography and, if the conversion was incomplete, a further 2.5 g (8 mmol) of 3-chloroperbenzoic acid were added. 100 g of water were added 4 hours later and the mixture was neutralized with sodium hydrogencarbonate solution. The phases were separated, the aqueous phase was extracted with dichloromethane and the solvent was distilled off. The residue was boiled for 4 h with 100 g of 70% sulfuric acid and then poured on to 200 g of ice. Extraction and crystallization gave 1.15 g (7.5 mmol, 5%) of 2-methyl-4-fluorobenzoic acid. If the reaction is carried out under these conditions with 9.2 g (15 mmol) of ®Oxone (= potassium peroxomonosulfate) instead of with 3-chloroperbenzoic acid, essentially the same result is obtained.

EXAMPLE 23

12.4 g (0.05 mol) of 2-chloro-4-fluoro-4'-methylbenzophenone in 30 ml of tetrahydrofuran were added dropwise to a solution of 19.0 g (0.1 mol) of toluene-4-sulfonic acid hydrate and 3.8 g (0.1 mol) of 90% hydrogen peroxide in 100 ml of tetrahydrofuran. The mixture was subsequently stirred for 12 h at 20° C. and then diluted with 100 g of water. Further processing as described in Example 22 gave 7.6 g (43.5 mmol, 87%) of 2-chloro-4-fluorobenzoic acid (m.p. 181°–186° C.).

EXAMPLE 24

7.6 g (25mmol) of 2,4,5-trichloro-2'-fluorobenzophenone, 4.3 g (0.115 mol) of 90% hydrogen peroxide and 0.25 g of 2-nitrobenzoselenic acid were stirred for 24 h in 50 ml of dichloromethane. The insoluble constituents were then filtered off, water was added and the organic phase was separated off. After removal of the solvent, the residue was heated with 120 g of 60% sulfuric acid for 8 h to hydrolyze the ester present. 1.55 g (13.8 mmol, 55%) of 2-fluorophenol could then be separated off by steam distillation. 4.8 g (21 mmol, 85%) of 2,4,5-trichlorobenzoic acid (crude (GC) ca. 95%) were isolated from the mother liquor.

EXAMPLE 25

2.5 g of sodium percarbonate were added over 1 h to a solution of 2.2 g (10 mmol) of 3,4-difluorobenzophenone and 20 ml of trifluoroacetic acid (0° C.) and the temperature was then allowed to rise to 20° C. The mixture was stirred for 16 h at this temperature and 50 g of ice were then added. The mixture was subsequently extracted twice with dichloromethane and the organic phases were washed (NaHCO$_3$) until the washings were neutral. The solvent was then removed. Working-up as described in Example 22 gave 1.2 g (7.6 mmol, 76%) of 3,4-difluorobenzoic acid, which can be obtained analytically pure from water (melting point 113°–120.5° C.).

EXAMPLE 26

6.0 g (25 mmol) of 3,5-dinitroperbenzoic acid (95%), 0.1 g of 4,4'-thiobis(6-tert-butyl-3-methylphenol) and 3.37 g (10 mmol) of 2,3,4,5-tetrachloro-2'(4')-fluorobenzophenone (mixture of isomers) were refluxed for 8 h in 50 ml of 1,2-dichloroethane. The mixture was then cooled in an ice bath and diluted with 100 ml of 1,2-dichloroethane. After careful washing of the organic phase with sodium hydrogencarbonate solution until the washings were neutral, the solvent was removed. The residue was worked up further as described in Example 24 to give 1.2 g of 2(4)-fluorophenol (crude mixture, separation by fractionation) and 2.1 g (8.1 mmol, 81%) of 2,3,4,5-tetrachlorobenzoic acid.

What is claimed is:

1. A process for the preparation of halogenated benzoic acids of general formula (I):

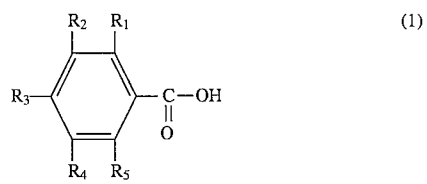

in which $R_1$, $R_2$, $R_3$, $R_4$ and $R_5$ are hydrogen, fluorine, chlorine or bromine atoms or $C_1$-$C_6$- alkyl, $C_1$-$C_6$-alkoxy, nitro, cyano, trifluoromethyl, aidehyde, $C_1$-$C_4$-alkoxycarbonyl, -SO$_2$-$C_1$-$C_4$-alkyl, -SO$_2$-phenyl, -CONH$_2$, -CON($C_1$-$C_4$-alkyl)$_2$, hydroxy, carboxy, -NH$_2$ or -N($C_1$-$C_4$- alkyl)$_2$ groups, at least one of the substituents $R_1$–$R_5$ being one of said halogen atoms, which comprises the step of:

reacting 1 mol of the benzophenone, asymmetrically substituted on the benzene rings A and B, of general formula (2):

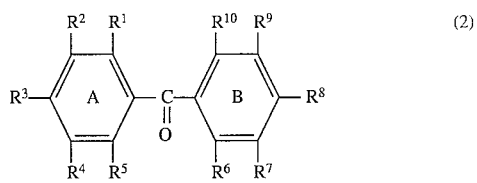

in which $R^1$–$R^{10}$ are as defined above for $R_1$–$R_5$, and in which the number of electron-attracting radicals in the ring A is at least 1 greater than the number of electron-attracting radicals minus the number of alkyl or alkoxy groups, in the ring B with about 1 to about 10 mol of an oxidizing agent selected from the group, consisting of hydrogen peroxide, urea/hydrogen peroxide addition product, an alkali metal peroxide, ammonium, alkali metal or alkaline earth metal peroxodisulfates, pertungstates, perberates or percarbonates, ozone, alkyl- or aryl-percarboxylic acids, alkyl- or arylpersulfonic acids, and persulfuric acid, at temperatures from about −20° to about +100°.

2. The process as claimed in claim 1, wherein the reaction is carried out at temperatures from about 0° C. to about 70° C.

3. The process as claimed in claim 1, wherein the reaction is carried out at temperatures from about 20° C. to about 60° C.

4. The process as claimed in claim 1 wherein the reaction is carried out with sodium, potassium or ammonium peroxodisulfate, sodium percarbonate, performic acid, peracetic acid, trifluoroperacetic acid, hexafluoropropanepersulfonic acid, 3-chloroperbenzoic acid, 3,5-dinitroperbenzoic acid, magnesium monoperphthalate, methanepersulfonic acid, trifluoromethanepersulfonic acid or p-toluenepersulfonic acid.

5. The process as claimed in claim 1, wherein the reaction is carried out in the presence of sulfuric acid having a concentration of about 80 percent by weight to about 20 percent by weight oleum, hydrogen fluoride, an aliphatic carboxylic acid having 1 to 6 carbon atoms which can be substituted by halogen atoms in the alkyl radical, an alkylsulfonic acid having 1 to 6 carbon atoms which can be substituted by halogen atoms in the alkyl radical, or acetic anhydride.

6. The process as claimed in claim 1, wherein the reaction is carried out in the presence of dichloromethane, trichloromethane, 1,2-dichloroethane, toluene, a xylene, chlorobenzene, dichlorobenzene, chlorotoluene or dichlorotoluene.

7. The process as claimed in claim 1, wherein the reaction is carried out with an approximately 10 to approximately 90% aqueous hydrogen peroxide solution.

8. The process as claimed in claim 1, wherein the reaction is carried out with an approximately 25 to approximately 50% aqueous hydrogen peroxide solution.

9. The process as claimed in claim 1, wherein the reaction is carried out with an aqueous hydrogen peroxide solution in about 80 percent by weight sulfuric acid to about 20 percent by weight oleum.

10. The process as claimed in claim 1, wherein the reaction is carried out with an aqueous hydrogen peroxide solution in about 95 percent by weight sulfuric acid to about 5 percent by weight oleum.

11. The process as claimed in claim 1, wherein about 200 to about 2000 percent by weight of sulfuric acid, based on the benzophenone starting compound, are used in the reaction with aqueous hydrogen peroxide solution in sulfuric acid or oleum.

12. The process as claimed in claim 1, wherein peracids are used as oxidizing agents and, are prepared in situ by reacting one or more acids with aqueous hydrogen peroxide solution, alkali metal or alkaline earth metal peroxodisulfates, pertungstates, perborates or percarbonates, ozone or sodium peroxide.

13. The process as claimed in claim 1, wherein any halogenated phenyl benzoates formed as intermediates are hydrolyzed to the halogenated benzoic acids in situ or after intermediate isolation and/or purification.

14. The process as claimed in claim 1, wherein the reaction is carried out in the presence of fluoride-trapping compounds.

15. The process as claimed in claim 1, wherein the reaction is carried out in the presence of calcium salts or silicon dioxide as fluoride-trapping compounds.

16. The process as claimed in claim 1, wherein phenols of general formula (3):

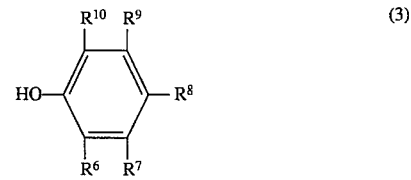

in which $R^6$–$R^{10}$ are as defined in claim 1, at least one of the substituents $R^6$–$R^{10}$ being a fluorine atom, are obtained in addition to the compounds of general formula (1) given in claim 1.

* * * * *